US010183235B2

(12) United States Patent
Humphrey (10) Patent No.: US 10,183,235 B2
(45) Date of Patent: Jan. 22, 2019

(54) COMPOSITIONS AND METHODS FOR THE LIQUID-PHASE SEPARATION OF ISOMERS OF AROMATIC MOLECULES

(71) Applicant: BOARD OF REGENTS, THE UNIVERSITY OF TEXAS SYSTEM, Austin, TX (US)

(72) Inventor: Simon M. Humphrey, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 3 days.

(21) Appl. No.: 15/532,647

(22) PCT Filed: Nov. 25, 2015

(86) PCT No.: PCT/US2015/062585
§ 371 (c)(1),
(2) Date: Jun. 2, 2017

(87) PCT Pub. No.: WO2016/089686
PCT Pub. Date: Jun. 9, 2016

(65) Prior Publication Data
US 2017/0354902 A1  Dec. 14, 2017

Related U.S. Application Data

(60) Provisional application No. 62/088,194, filed on Dec. 5, 2014.

(51) Int. Cl.
| | |
|---|---|
| *B01D 15/08* | (2006.01) |
| *B01J 20/22* | (2006.01) |
| *B01J 20/28* | (2006.01) |
| *C07C 7/12* | (2006.01) |
| *C07C 5/44* | (2006.01) |
| *B01D 17/02* | (2006.01) |
| *C07C 15/44* | (2006.01) |

(52) U.S. Cl.
CPC ......... *B01D 15/08* (2013.01); *B01D 17/0202* (2013.01); *B01J 20/226* (2013.01);
(Continued)

(58) Field of Classification Search
CPC .......... C07C 15/44; C07C 7/12; B01D 15/08; B01D 17/0202; B01J 20/226;
(Continued)

(56) References Cited

U.S. PATENT DOCUMENTS

| | | |
|---|---|---|
| 7,879,221 B2 | 2/2011 | Putter et al. |
| 7,910,732 B2 | 3/2011 | Schubert et al. |

(Continued)

OTHER PUBLICATIONS

International Search Report and Written Opinion issued in Application No. PCTUS2015062585, dated Feb. 9, 2016.
(Continued)

*Primary Examiner* — John Kim
(74) *Attorney, Agent, or Firm* — Meunier Carlin & Curfman LLC (57) ABSTRACT

The present invention includes a composition and process for separating p-isomers of vinylbenzenes from a mixture of isomers comprising the steps of: providing a porous microwaved Mg(II) 2,4-pyridinedicarboxylic acid coordination polymer having a 1-D pore structure and showing reversible soft-crystal behavior by preferentially binding p-isomers of vinylbenzene; adding a mixture of vinylbenzenes isomers to the porous microwaved Mg (II) 2,4-pyridinedicarboxylic acid coordination polymer; adsorbing the p-isomers of vinylbenzene from the mixture of vinylbenzenes isomers; selectively adsorb the p-isomers of vinylbenzene in the 1-D pore structure; removing the mixture of vinylbenzenes isomers; and desorbing the p-isomers of vinylbenzene from the 1-D pore structure to purify the p-isomers of vinylbenzene.

18 Claims, 3 Drawing Sheets

(52) U.S. Cl.
CPC ... *B01J 20/28011* (2013.01); *B01J 20/28016* (2013.01); *B01J 20/28064* (2013.01); *B01J 20/28083* (2013.01); *C07C 7/12* (2013.01); *C07C 15/44* (2013.01)

(58) Field of Classification Search
CPC ............ B01J 20/28011; B01J 20/28016; B01J 20/28064; B01J 20/28083
See application file for complete search history.

(56) References Cited

U.S. PATENT DOCUMENTS

| | | | |
|---|---|---|---|
| 2011/0010826 A1* | 1/2011 | Kaskel | A62D 5/00 2/457 |
| 2011/0138999 A1 | 6/2011 | Willis | |
| 2013/0129608 A1 | 5/2013 | Watanabe et al. | |

OTHER PUBLICATIONS

Saccoccia et al., Separation of p-divinylbenzene by selective room-temperature adsorption inside Mg-CUK-1 prepared by aqueous microwave synthesis. Angew Chem Int Ed Engl. Apr. 27, 2015;54(18):5394-8.

Yoon, et al., Gas-Sorption selectivity of CUK-1: A porous coordination solid made of cobalt (II) and pyridine-2,4-dicarboxylic acid, Adv. Mat. 2007, 19, 1830-1834.

Gu, et al., Metal-organic framework MIL-101 for high-resolution gas-chromatographic separation of xylene isomers and ethylbenzene, Angew. Chem. Int. Ed. 2010, 49, 1477-1480.

International Preliminary Report on Patentability issued in Application No. PCTUS2015062585, dated Jun. 15, 2017.

* cited by examiner

COMPOSITIONS AND METHODS FOR THE LIQUID-PHASE SEPARATION OF ISOMERS OF AROMATIC MOLECULES

CROSS-REFERENCE TO RELATED APPLICATIONS

This application is a national stage application filed under 35 U.S.C. § 371 of PCT/US2015/062585 filed Nov. 25, 2015, which claims the benefit of and priority to U.S. Provisional Application No. 62/088,194 filed on Dec. 5, 2014, the disclosures of which are expressly incorporated herein by reference in their entireties.

TECHNICAL FIELD OF THE INVENTION

The present invention relates in general to the field of liquid-phase separation, and more particularly, to the separation of p-divinylbenzene by selective room-temperature adsorption inside Mg-CUK-1 prepared by aqueous microwave synthesis.

BACKGROUND OF THE INVENTION

Without limiting the scope of the invention, its background is described in connection with liquid-phase separations of organic isomers by selective room-temperature adsorption using Mg-CUK-1 prepared by aqueous microwave synthesis.

A number of porous coordination polymers (PCPs) have been shown to possess the ability to effectively separate complex mixtures of gases and less commonly, mixtures of liquid hydrocarbons. The latter represents a tangible application for such materials, especially to achieve separations that cannot be easily performed using common large-scale separation methods (e.g., column chromatography, ion exchange, fractional distillation). One such example concerns the separation of isomers of divinylbenzene (DVB): p-DVB is important in the manufacture of cross-linked styrene polymers, which, paradoxically, are utilized in the manufacture of ion exchange resins. DVB is prepared by dehydrogenation of crude o-, m- and p-isomer mixtures of diethylbenzene. Commercially-available DVB consists of approximately 80% m-DVB and p-DVB along with the products of partial dehydrogenation, m- and p-ethylvinylbenzene (EVB) and naphthalene. From an industrial standpoint, pure p-DVB is most preferred for the formation of ordered cross-linked styrene/p-DVB copolymers, but large-scale separation approaches have proven to be inefficient.

U.S. Pat. No. 7,910,732, entitled "Method for producing porous metal-organic framework materials," discloses processes for preparing a porous metal-organic framework comprising at least two organic compounds coordinated to at least one metal ion, the porous metal-organic frameworks prepared by the process and their use, in particular for gas storage and gas separation.

U.S. Pat. No. 7,879,221, entitled "Process for preparing porous metal organic frameworks," discloses a process for preparing a porous metal organic framework comprising at least two organic compounds coordinated to at least one metal ion, which comprises the steps (a) oxidation of at least one anode comprising the metal corresponding to at least one metal ion in a reaction medium in the presence of at least one first organic compound which is an optionally substituted monocyclic, bicyclic or polycyclic saturated or unsaturated hydrocarbon in which at least two ring carbons have been replaced by heteroatoms selected from the group consisting of N, O and S to form a reaction intermediate comprising the at least one metal ion and the first organic compound; and (b) reaction of the reaction intermediate at a prescribed temperature with at least one second organic compound which coordinates to the at least one metal ion, with the second organic compound being derived from a dicarboxylic, tricarboxylic or tetracarboxylic acid.

U.S. patent application Ser. No. 2013/0129608 entitled "Porous coordination polymer, process for producing same, gas storage method, and gas separation method," discloses a porous coordination polymer that includes metal complexes formed by coordination bonding between a trivalent metal ion and an aromatic tricarboxylic acid. The porous coordination polymer also has a pore structure formed by integration of a plurality of the metal complexes. The entire contents of each of which are incorporated herein by reference.

U.S. Patent Application Publication No. 2011/0138999 entitled "Metal organic framework polymer mixed matrix membranes," discloses a metal-organic framework (MOF)-polymer mixed matrix membranes (MOF-MMMs) prepared by dispersing high surface area MOFs into a polymer matrix. The MOFs allow the polymer to infiltrate the pores of the MOFs, which improves the interfacial and mechanical properties of the polymer and in turn affects permeability for gas separation applications such as $CO_2$ removal from natural gas. The entire contents of each of which are incorporated herein by reference.

SUMMARY OF THE INVENTION

The present invention provides a process for separating p-isomers of divinylbenzenes from a mixture of isomers comprising the steps of: providing a porous coordination polymer material based on Mg(II) and 2,4-pyridinedicarboxylic acid with a 1-D pore structure, obtained by an aqueous microwave-assisted method, and showing reversible soft-crystal behavior by preferentially binding p-isomers of DVB; adding a commercially-available mixture of DVB and EVB isomers to the porous microwaved Mg(II)/2,4-pyridinedicarboxylate coordination polymer; adsorbing the p-isomers of DVB from the crude mixture of isomers; adsorb the p-isomers of DVB in an ordered repeating close-packed fashion within the 1-D pore structure; removing the mixture of m-DVB-enriched isomers; and, desorbing the p-isomers of DVB from the 1-D pore structure to obtain pure p-DVB. The vinylbenzene may be divinylbenzene, ethylvinylbenzene or both. The mixture of vinylbenzenes isomers may be p-isomers, o-isomers, and m-isomers; p-isomers and o-isomers; or p-isomers and m-isomers.

The present invention provides a process for separating isomers from a mixture comprising the steps of: providing a porous microwaved Mg(II) coordination polymer having a 1-D pore structure showing reversible soft-crystal behavior by preferentially binding one or more organic isomers; adding a mixture of organic isomers to the porous microwaved Mg(II) coordination polymer; adsorbing a p-isomer from the mixture of organic isomers; selectively adsorb the p-isomer inside the 1-D pore structure; removing the p-isomer-depleted mixture of organic isomers; and desorbing the p-isomer from the 1-D pore structure to purify the one isomer. The porous microwaved Mg(II) coordination polymer may be a Mg(II) 2,4-pyridinedicarboxylic acid coordination polymer. The porous microwaved Mg(II) coordination polymer selectively adsorbs one or more organic molecule isomers which crystallize inside the pores at ambient temperature and pressure. The organic molecules may be pyridine, benzene, xylene, ethylvinylbenzene, divinylbenzene or a combination thereof. The p-isomer may be p-xylene, p-ethylvinylbenzene, p-divinylbenzene or a combination thereof. The o-xylene, m-xylene, o-divinylbenzene, m-divinylbenzene, o-ethylvinylbenzene and m-ethylvinylbenzene are selectively excluded from the porous microwaved Mg(II) coordination polymer.

The present invention provides a method of making a porous Mg(II) coordination polymer comprising the steps of: providing a reaction chamber containing $Mg(NO_3)xH_2O$ hydrate in $H_2O$; adding 2,4-pyridinedicarboxylic acid and KOH to the reaction chamber; exposing the reaction chamber to microwaves; cooling the reaction chamber to form a crystalline solid; and purifying the crystalline solid to form a porous microwaved Mg(II)/2,4-pyridinedicarboxylic acid coordination polymer.

The present invention provides a method of making a porous Mg(II) coordination polymer comprising the steps of: providing a reaction chamber containing Mg(II) complex in water; adding 2,4-pyridinedicarboxylic acid to the Mg(II) complex; exposing the reaction chamber to microwaves; cooling the reaction chamber to form a crystalline solid; and purifying the crystalline solid to form a porous microwaved Mg(II) coordination polymer, wherein the porous microwaved Mg(II) coordination polymer selectively adsorbs one or more organic molecule isomers, which crystallize inside the pores at ambient temperature and pressure. The organic molecule isomers may be the p-isomers, e.g., p-xylene, p-ethylvinylbenzene, p-divinylbenzene or a combination thereof. The organic molecules may be pyridine, benzene, xylene, ethylvinylbenzene, divinylbenzene or a combination thereof. O-xylene, m-xylene, o-divinylbenzene, m-divinylbenzene, o-ethylvinylbenzene and m-ethylvinylbenzene are selectively excluded from the porous microwaved Mg(II) coordination polymer.

The present invention provides a porous coordination polymer comprising: infinite arrays of metal complexes formed by coordination bonding between a divalent Mg ion and an aromatic dicarboxylic acid, wherein the porous coordination polymer has a pore structure formed by integration of a plurality of the metal complexes that selectively adsorbs a p-isomer of an organic molecule. The divalent metal ion may be Mg(II) and the aromatic dicarboxylic acid may be 2,4-pyridinedicarboxylic acid. The pore structure may have a diameter of between 1-2 nm.

A porous Mg(II) coordination polymer comprising: metal complexes formed by coordination bonding between a Mg(II) ion and an 2,4-pyridinedicarboxylic acid, wherein the porous Mg(II) coordination polymer has a pore structure having a diameter of about 2 nm formed by integration of a plurality of the metal complexes that selectively bind a p-isomer of an organic molecule.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A number of porous coordination polymers (PCPs) have been shown to possess the ability to effectively separate complex mixtures of gases and less commonly, mixtures of liquid hydrocarbons. The latter represents a tangible application for such materials, especially to achieve separations that cannot be easily performed using common large-scale separation methods (e.g., column chromatography, ion exchange, fractional distillation). One such example concerns the separation of isomers of DVB: p-DVB is important in the manufacture of cross-linked styrene polymers, which, paradoxically, are utilized in the manufacture of ion exchange resins. DVB is prepared by dehydrogenation of crude o-, m- and p-isomer mixtures of diethylbenzene. Commercially-available DVB consists of approximately 80% m- and p-DVB along with the products of partial dehydrogenation, m- and p-ethylvinylbenzene (EVB). From an industrial standpoint, pure p-DVB is most preferred for the formation of ordered cross-linked styrene/p-DVB copolymers, but large-scale separation approaches have proven to be inefficient.

A new Mg(II)-based version of the porous coordination polymer CUK-1 with 1-D pore structure was prepared by microwave synthesis in water. Mg-CUK-1 is moisture-stable, thermally stable up to 500° C., and shows unusual reversible soft-crystal behavior: dehydrated single crystals of the material selectively adsorb a range of organic molecules, which crystallize inside the pores at ambient temperature and pressure. Both polar and apolar aromatics including pyridine, benzene, p-xylene and p-divinylbenzene (DVB) are all readily adsorbed by Mg-CUK-1, while other isomers from complex mixtures of xylenes or DVBs are selectively excluded. The solvent-loaded structures have been studied by single crystal X-ray diffraction. Time-dependent liquid sorption experiments using commercially-available DVB demonstrates a high and rapid selective adsorption of p-DVB and exclusion of m-DVB and ethylvinylbenzene isomers.

The present invention provides a Mg(II)-based version of the porous coordination polymer CUK-1 with 1-D pore structure was prepared by microwave synthesis in water.

Mg-CUK-1 is moisture-stable, thermally stable up to 500° C., and shows unusual reversible soft-crystal behavior where dehydrated single crystals of the material selectively adsorb a range of organic molecules, which crystallize inside the pores at ambient temperature and pressure. Both polar and apolar aromatics including pyridine, benzene, p-xylene and p-divinylbenzene (DVB) are all readily adsorbed by Mg-CUK-1, while other isomers from complex mixtures of xylenes or DVBs are selectively excluded. The solvent-loaded structures have been studied by single crystal X-ray diffraction. Time-dependent liquid sorption experiments using commercially-available DVB demonstrates a high and rapid selective adsorption of p-DVB and exclusion of m-DVB and ethylvinylbenzene isomers.

The present invention provides a new porous material synthesized using cheap and non-toxic materials, using a scalable microwave-assisted chemical method. The material is synthesized in water as the only solvent. The resulting product has been finely structurally characterized and has an infinite 1-D pore structure, in which the micro-pores have an accessible diameter of approximately 2 nm. These pores are highly selective for the absorption of certain 'guest' molecules, such as particular organic molecules from crude mixtures, via a direct liquid-solid extraction mechanism. In particular, the material is highly selective for the rapid uptake of p-divinylbenzene from crude commercially-available mixtures that contain only 40-80% of that molecule. The selectivity has been studied in an in-depth structural sense by recovery of the X-ray structure of the p-divinylbenzene-loaded material, which confirms the efficacy of the material.

The present invention provides for rapid, microwave-assisted synthesis in water, using only Mg(II) (non-toxic) as the metal precursor. Some related materials are known and have even been industrially scaled-up (e.g. see 'MOF-5' and 'MOF-177' as produced for gas separations on a ton scale). To date, no such material has been shown to have high selectivity for one isomer of divinylbenzene (DVB). DVB is used on a massive scale industrially for the synthesis of cross-linked poly(styrenes) for use as exchange resins and similar applications. Currently, use of the crude mixtures (containing 4 or more related isomers that arise from the synthesis of the target p-DVB) is tolerated because no cost-efficient separation process exists.

The present invention provides higher selectivity between isomers; faster separation; due to synthesis method and cheapness of precursors, it is possible to manufacture large quantities and easily fabricate columns for continuous flow separations.

The present invention provides precursor materials that include magnesium(II) nitrate; and 2,4-pyridine dicarboxylic acid. Other examples include 1,2-cyclohexane dicarboxylic acid, 1,3-cyclohexane dicarboxylic acid, 1,4-cyclohexane dicarboxylic acid, 1,1-cyclopropane dicarboxylic acid, 1,1-cyclobutane dicarboxylic acid, 1,3-cyclopentane dicarboxylic acid or the like; 2,5-norbornane dicarboxylic acid, 1,3-adamantane dicarboxylic acid, 1,3-cyclohexane dicarboxylic acid, 1,4-cyclohexane dicarboxylic acid, 1,3-cyclohexane dicarboxylic acid, terephthalic acid, isophthalic acid, phthalic acid, 2,5-dimethylterephthalic acid, 2,3-pyridine dicarboxylic acid, 2,4-pyridine dicarboxylic acid, 2,6-pyridine dicarboxylic acid, 3,4-pyridine dicarboxylic acid, 3,5-pyridine dicarboxylic acid, 4,4'-biphenyldicarboxylic acid, 2,2'-biphenyldicarboxylic acid, 4,4'-diphenyl ether dicarboxylic acid, 4,4'-diphenyl methane dicarboxylic acid, 4,4'-diphenyl sulfone dicarboxylic acid, 1,2-naphthalene dicarboxylic acid, 1,4-naphthalene dicarboxylic acid, 1,5-naphthalene dicarboxylic acid, 2,3-naphthalene dicarboxylic acid, 2,6-naphthalene dicarboxylic acid, 2,7-naphthalene dicarboxylic acid, and 1,8-anthracene dicarboxylic acid. Moreover, these dicarboxylic acids and derivatives thereof may be used alone or in a combination of two or more.

The present invention provides a new Mg(II)-based version of the porous coordination polymer CUK-1 with 1-D pore structure prepared by microwave synthesis in basic water. Mg-CUK-1 is moisture-stable, thermally stable up to 500° C., and shows unusual reversible soft-crystal behavior: dehydrated single crystals of the material selectively adsorb a range of small molecules, which become ordered inside the pores at ambient temperature and pressure. Both polar and apolar aromatics, including pyridine, benzene, p-xylene and p-divinylbenzene, are all readily adsorbed by Mg-CUK-1, while, o- and m-isomers from crude mixtures of xylenes and divinylbenzenes are selectively excluded.

Highly porous cobalt(II)-based coordination polymer named CUK-1, which has received significant attention due to its exceptional separation ability of complex gas mixtures. CUK-1 is based on 2,4-pyridinedicarboxylic acid (2,4-pdc) and contains 1-D channels with square pore windows. The material was shown to be highly robust, owing to the presence of infinite 1-D metal hydroxide chains that support a corrugated wall structure. One potential drawback of the original CUK-1 material pertains to the reactivity of Co-OH bonds in the presence of ambient moisture. Ongoing efforts to determine methods for the preparation of CUK-1 using alternative metals have ultimately yielded a fast, reproducible and high-yielding method for the production of a Mg(II) analogue, prepared using only water as solvent via a rapid, and energy efficient microwave (μW)-assisted method that provides a crystalline structure.

Figure 1A:
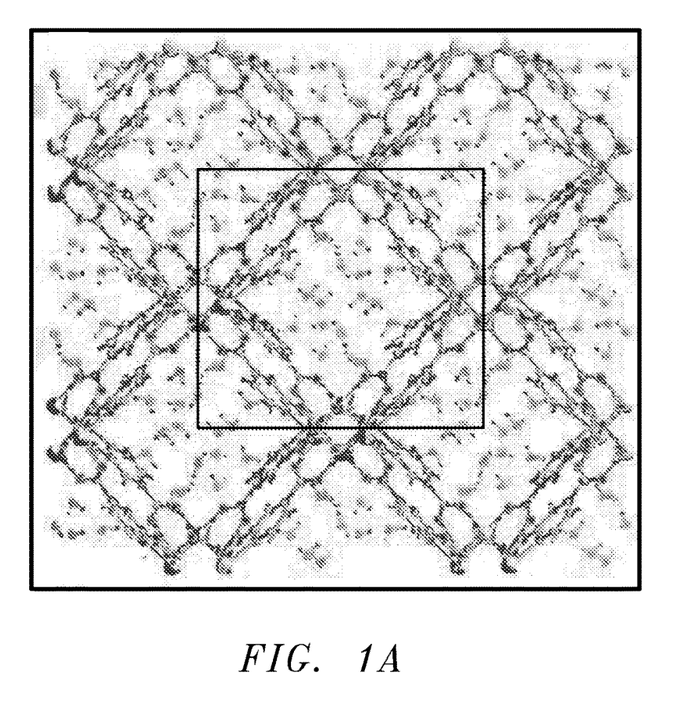
FIG. 1A is an image showing the structure of Mg-CUK-1.
Figure 1B:
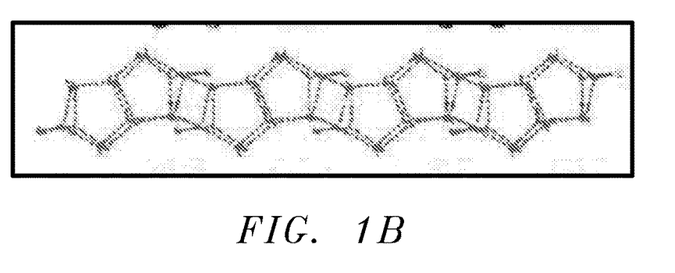
FIG. 1B is an image of a single chain of H-bonded $H_2O$ molecules that form pentameric drums.
Figure 1C:
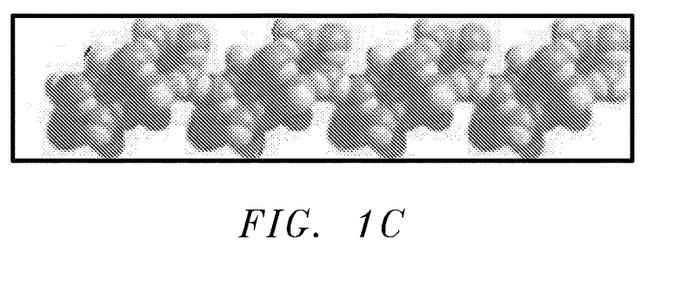
FIG. 1C is a space-filling view of a single $H_2O$ chain, depicting the "lumpy" channel topology.

FIG. 1A is an image showing the structure of Mg-CUK-1 viewed down the crystallographic a-axis; solvent 0-atoms are drawn in yellow for clarity. FIG. 1B is an image of a single chain of H-bonded $H_2O$ molecules that form pentameric drums. FIG. 1C is a space-filling view of a single $H_2O$ chain, depicting the "lumpy" channel topology. Replacement of Co(II) with Mg(II) because the resulting Mg-CUK-1 is significantly (19.2%) lighter than the original material and is thermally and chemically more stable due to the increased hardness of Mg(II) ions. The Mg analogue can also be prepared using a conventionally-heated method at 220° C. in $H_2O$ for 15 hours. Although the average crystallite size obtained from conventional (Cv) heating is slightly larger, the reaction yield and the bulk textural properties are both superior for material obtained from the μw-assisted method (vide infra). The Mg(II) centers in Mg-CUK-1 are octahedrally coordinated and bridge into infinite chains of edge- and vertex-sharing $Mg_3OH$ triangles. The lattice connectivity of Mg-CU K-1 is identical to that of Co-CUK-1, but surprisingly the space group of the as-synthesized material was found to be lower symmetry ($P2_1/c$ versus C2/c). The lower symmetry of this new material arises due to the positions of guest $H_2O$ solvent inside the channels. A network of close-range H-bonding interactions that includes $\mu_3$-OH moieties in the pore walls results in the formation of a remarkably well-ordered pseudo-ice phase at room temperature; the solvent is so well ordered that all H-atoms were directly located in the peak difference map. Full resolution of the structure reveals an infinite chain of $H_2O$ cages comprised of face-sharing pentameric drums FIGS. 1B and 1C. H·O contact distances lie in the range 2.71-2.96 A compared with 2.76 A in the lh-phase of ice. The extended 1-D 'ice' chains provide a perspective of the channel topology in Mg-CUK-1, which take the form of undulating channels that contain pockets linked by smaller apertures. Despite the extended H-bonding network, Mg-CUK-1 is easily completely dehydrated by gentle heating (50° C.) in vacuum over 1 hour, or alternatively at ambient pressure using a stream of heated $N_2$ gas. Thermogravimetric analysis (TGA) confirms a rapid 22 wt % mass loss between 20 and 50° C. after which there is a very large window of stability until the onset of polymer degradation ca. 500° C. Heating a single crystal in a stream of dry N.2 and subsequent in situ X-ray diffraction analysis at 100° C. revealed complete dehydration accompanied by retention of 3-D order. Notably, the symmetry spontaneously changes to C2/c upon dehydration. In comparison to the as-synthesized structure, dehydrated crystals undergo a concertina distortion perpendicular to the direction of channel propagation, resulting in diamondoid-shaped channels Cooling of a dehydrated crystal to −143° C. under dry $N_2$ did not result in further structural deformation (or reversion to the original primitive space group), which indicates that the concertinaing is simply due to loss of $H_2O$ from the pores and is not a temperature dependent phase transition. Dehydrated Mg-CUK-1 is highly stable when stored in air and when re-suspended in fresh $H_2O$, as confirmed by bulk powder X-ray diffraction analysis (PXRD). The bulk textural properties of the material were assessed as a function of the synthesis method, using a number of small molecule probe gases in the range 0-1 atm. Regardless of the heating method, Mg-CUK-1 shows a marked adsorption preference of $CO_2$ and $H_2$ over $N_2$ and $CH_4$, as observed for the Co(II)-based analogue. The total sorption capacities and estimated $CO_2$ BET surface area of μw-Mg-CUK-1 were found to be significantly higher than for Cv-Mg-CUK-1 for all gases studied, especially for $H_2$. The table below shows a summary of gas adsorption properties of Mg-CUK-1 as a function of synthesis method.

| Synthesis method | $S_{CO_2}^{BET}$ ($m^2 g^{-1}$) | $V_{N_2}$ ($cm^3 g^{-1}$) | $V_{CO_2}$ ($cm^3 g^{-1}$) | $V_{H_2}$ ($cm^3 g^{-1}$) | $V_{CH_4}$ ($cm^3 g^{-1}$) |
|---|---|---|---|---|---|
| μw | 602 | 68 | 196 | 143 | 95 |
| Cv | 581 | 32 | 165 | 60 | 84 |

Fast crystallization under μw heating results in only slightly smaller crystallites, so this should not account for the difference in observed capacities. It is plausible that pore blocking due to unreacted organic and inorganic components may be less prevalent from the μw route.

Figure 2A:
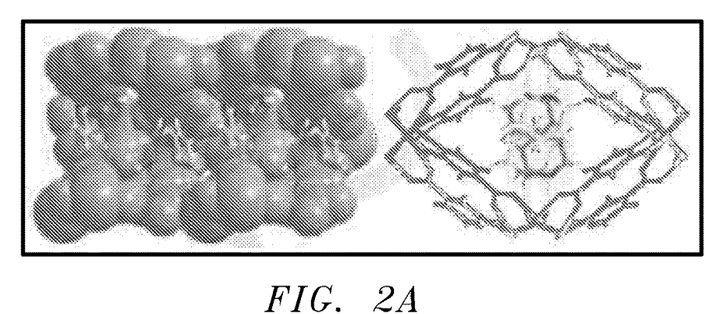
FIGS. 2A-2E show crystal structures of solvent-loaded Mg-CUK-1.
Figure 2B:
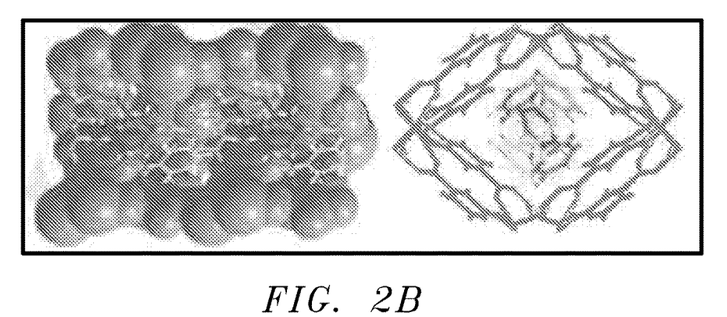
Figure 2C:
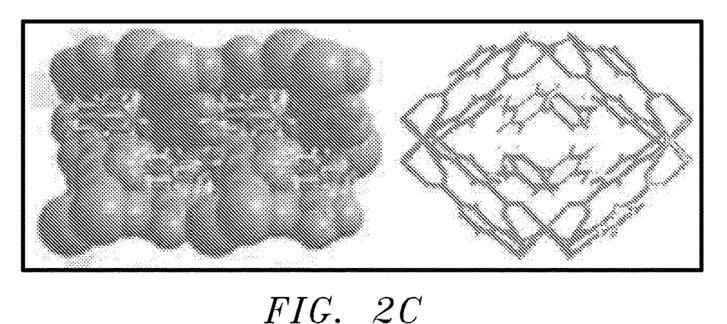
Figure 2D:
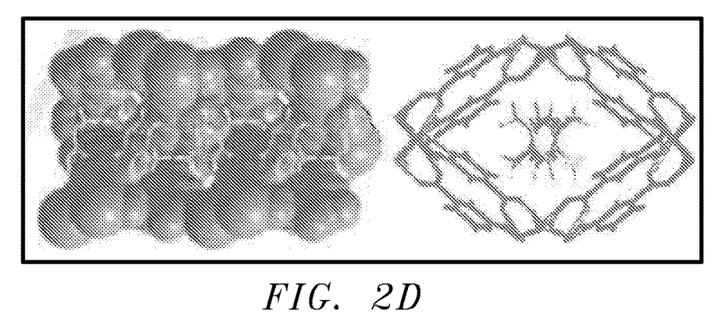
Figure 2E:
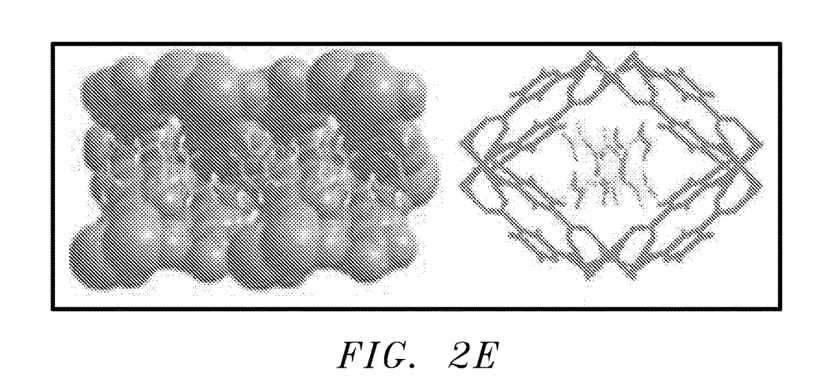
Figure 2F:
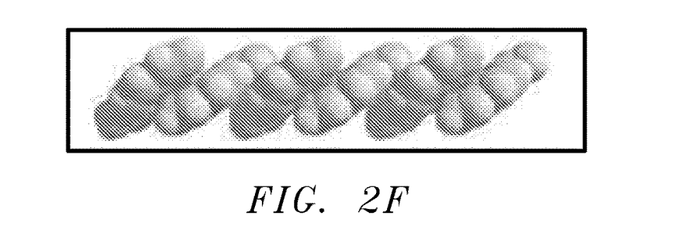
FIG. 2F is a space fill model of the packing arrangement of a single chain of p-DVB monomers.
Figure 3:
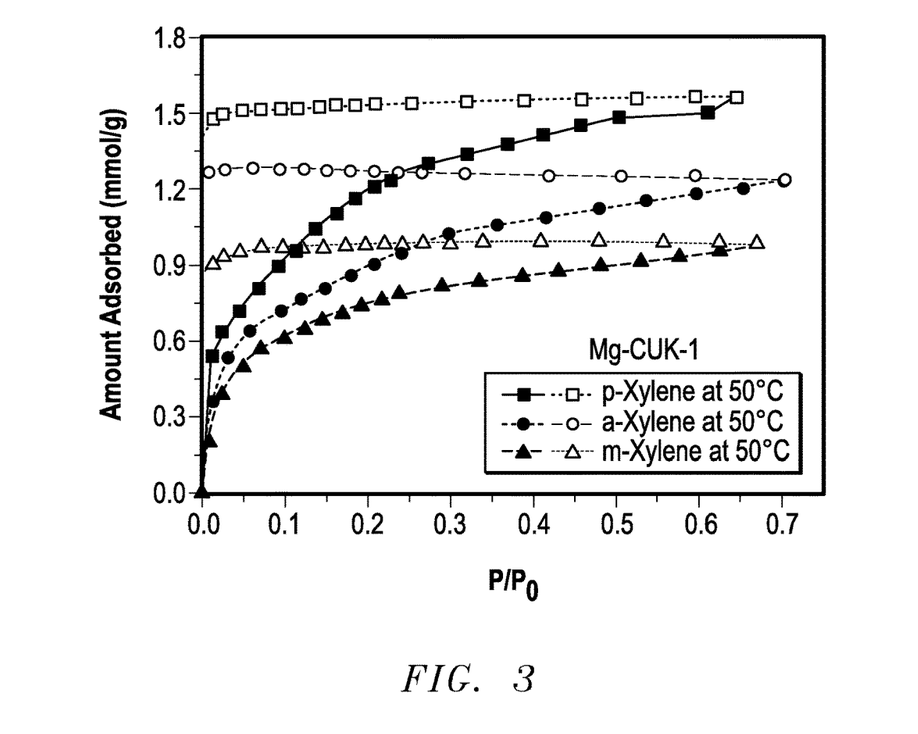
FIG. 3 is a graph of the liquid absorption-desorption profiles for the three xylenes isomers in dehydrated Mg-CUK-1.

FIGS. 2A-2E show crystal structures of solvent-loaded Mg-CUK-1. The polymer is drawn in grey and all crystallographically-unique solvent positions are shown in different colors. Top to bottom: FIG. 2A shows pyridine; FIG. 2B shows benzene; FIG. 2C shows toluene; FIG. 2D shows p-xylene; FIG. 2E shows p-divinylbenzene absorbed from a crude mixture. FIG. 2F is a space fill model of the packing arrangement of a single chain of p-DVB monomers.

μw-Mg-CUK-1 provides selective adsorption/extraction of aromatic molecules from the liquid phase. Dehydrated crystallites were suspended in dry solvents over 1-5 days at room temperature. In all cases, individual crystals retained their crystallinity, allowing for the collection of new single crystal X-ray structures with ordered solvent molecules located inside the channels (see FIG. 2A-2E). In essence, Mg-CUK-1 facilitates the room-temperature crystallization of 1-D chains of aromatic molecules.

Absorption of pyridine inside dehydrated Mg-CUK-1 resulted in a zig-zag packing arrangement directed by short-range (2.52 Å) donor-acceptor contacts between pyridine-N and hydroxide-H atoms in the channel walls. Benzyl alcohol showed similar behavior. In contrast, apolar benzene crystallized to form an undulating ribbon with six unique (and partially occupied) orientations based on a combination of face-to-face host-guest π-π interactions (centroid-centroid=4.31 Å) and T-shaped H-π interactions (4.05 Å). Toluene formed a more simple ordered phase, with similar π-π interactions (centroid distance=4.30 Å). A handful of PCPs have been shown to selectively separate isomers of xylene. Interestingly, in this case only an ordered crystalline phase was obtained for p-xylene-treated Mg-CUK-1 single crystals treated with o- and m-xylene remained highly crystalline, but electron density corresponding to less than 1 $e^-$·per site was smeared throughout the centers of the channel voids. TGA and elemental microanalysis of the materials indicated at least some adsorption for all isomers. Liquid (vapor) sorption isotherms collected using each pure isomer in the range $p/p_o$=0-0.7 at 50° C. provides more valuable insight: it is apparent that dehydrated Mg-CUK-1 readily absorbs each isomer, but the relative capacity is of the order p>o>m. The minimum guest-accessible dimension of the pore openings in dehydrated Mg-CUK-1 is 8.0 Å obtained directly from the crystal structure. The critical diameters of the three xylenes isomers (o=6.6 Å, m=6.4 Å, p=5.7 Å) should permit easy access to the interior of the channels. Notably, the crystal structure of the p-isomer-loaded phase. The xylene-loaded material shows that guest-guest interactions are the dominant crystallization force, while close-range host-guest interactions that were dominant for smaller aromatics are not observed. Instead, head-to-tail type intermolecular $CH_3$-π guest-guest interactions are prevalent (centroid-C distance=4.24 Å).

Pure fractions of DVBs are not easily obtained, due to the aforementioned inherent purification issues. Instead, we directly treated a sample of dehydrated Mg-CUK-1 with a commercially available technical grade DVB, which contains >79% of a mixture of m- and p-DVB along with ≤21% of m- and p-EVB, naphthalene and 4-terl-butylcatechol stabilizer. To our unexpected surprise, after standing for 5 days, single crystals were found to contain only p. DVB (FIGS. 2A-2F). The packing arrangement of p-DVB is very similar to what was observed for p-xylene; guest-guest crystal packing interactions are clearly dominant. Individual p-DVB monomers are planar and tightly packed into 1-D chains with very close-range (3.63 Å) π-vinylene interactions. Kitagawa and co-workers previously studied selective DVB absorption and subsequent in situ polymerization by a terephthalate-based PCP with 1-D channels. They found that smaller channels selectively gave p-substituted polymers and it was concluded that the packing orientation of monomers inside the pores affected the extent of polymerization: a face-to-face orientation of monomers was thought to promote polymerization, but single crystal structures of the loaded materials were not obtained. This suggests that p-DVB is selectively absorbed inside 1-D channels because a head-to-tail orientation results in the most favorable enthalpy of crystallization. The critical diameters of all DVB and EVB isomers are similar to the corresponding xylene isomers, so it is possible for all molecules to enter the channels. There are therefore two plausible explanations for the impressive selective absorption observed: (a) all isomers are initially absorbed into the channels, but p-DVB monomers eventually displace other isomers via a process of diffusion, due to dominant crystallization forces; (b) the inherent π-conjugation and extended resonance in the p-DVB isomer maintains a planar structure that can more easily enter the channels and undergo rapid crystallization with other monomers.

Synthesis of μw-Mg-CUK-1. 2,4-pyridinedicarboxylic acid (170 mg, 1.0 mmol) and KOH (2.0 M, 2.0 cm$^3$) in H$_2$O (2.0 cm$^3$) were added to a stirred solution of Mg(NO$_3$):z hydrate (380 mg, 1.5 mmol) in H$_2$O (3.0 cm$^3$) to give a viscous, opaque slurry, which was heated to 200° C. for 35 minutes in a MARS microwave (CEM Corp.) inside 100 cm$^3$ Teflon-lined Easy-Prep reaction vessels. The reaction temperature was monitored using a fiber-optic sensor. After cooling (30 minutes), the crystalline solid was purified by brief (3×20 s) cycles of sonication in fresh H$_2$O (20 cm$^3$), followed by decanting of the cloudy supernatant. Large, colourless prismatic crystals were isolated (average yield, 58 mg). Elemental analysis (%) calcd for $C_{14}HeMg_3N_zO_{10} \cdot 9H_2O$: C 28.1, H 4.38, N 4.68; found: C 28.2, H 4. 06, N 4.99.

Synthesis of Cv-Mg-CUK-1. The method described above was used to prepare the reaction slurry, which was alternatively transferred to a 23 cm$^3$ Teflon-lined autoclave (Parr Corp.), heated at 21° C. for 15 hours, and cooled for 6 hours, and purified as described above.

Dehydration and solvent loading. Bulk samples of Mg-CUK-1 purified as described above were evaporated to dryness in air, then dried further under vacuum at 50-60° C. for at least 2 hours. Elemental analysis (%) calcd for $C_{14}HeMg_3N_2O_{10}$: C 38.6, H 1.85, N 6.42; found: C 38.4, H 2.03, N 6 39. Longer evacuation times did not result in any sample degradation. Small quantities (5-10 mg) of dehydrated materials were transferred to scintillation vials under N$_2$ and covered with pre-dried solvents. The crystals were then left to stand for 2 days before analysis.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for separating p-isomers from a mixture comprising the steps of:
providing a porous microwaved Mg(II) 2,4-pyridinedicarboxylic acid coordination polymer having a 1-D pore structure showing reversible soft-crystal behavior by preferentially binding p-isomers;
adding a mixture of isomers of an organic molecule to the porous microwaved Mg (II) coordination polymer;
adsorbing the p-isomers from the mixture of organic molecule isomers;
crystallize the p-isomers in the 1-D pore structure;
removing the remaining mixture of organic molecule isomers; and
desorbing the p-isomers from the 1-D pore structure to purify the p-isomers.

2. The method of claim 1, wherein the mixture of isomers of the organic molecule comprises a mixture of vinylbenzene isomers.

3. The method of claim 2, wherein the vinylbenzene comprises divinylbenzene, ethylvinylbenzene or both.

4. The method of claim 2, wherein the mixture of vinylbenzene isomers comprises p-isomers, o-isomers, and m-isomers; p-isomers and o-isomers; or p-isomers and m-isomers.

5. The method of claim 1, wherein the porous microwaved Mg(II) 2,4-pyridinedicarboxylic acid coordination polymer selectively adsorbs p-isomers of the organic molecule, which crystallize inside the pores at ambient temperature and pressure.

6. The method of claim 1, wherein the organic molecule comprises pyridine, benzene, xylene, ethylvinylbenzene, divinylbenzene, or a combination thereof.

7. The method of claim 1, wherein the p-isomer is p-xylene, p-ethylvinylbenzene, p-divinylbenzene or a combination thereof.

8. The method of claim 1, wherein o-xylene, m-xylene, o-divinylbenzene, m-divinylbenzene, o-ethylvinylbenzene and m-ethylvinylbenzene are excluded from the porous microwaved Mg(II) 2,4-pyridinedicarboxylic acid coordination polymer.

9. A method of making a porous Mg(II) coordination polymer comprising the steps of:
providing a reaction chamber containing a Mg(II) complex in water;
adding 2,4-pyridinedicarboxylic acid to the Mg(II) complex;
exposing the reaction chamber to microwaves;
cooling the reaction chamber to form a crystalline solid; and
purifying the crystalline solid to form a porous microwaved Mg(II) coordination polymer, wherein the porous microwaved Mg(II) coordination polymer selectively adsorbs one or more organic molecule isomers, which crystallize inside the pores at ambient temperature and pressure.

10. The method of claim 9, wherein the Mg(II) complex comprises
$Mg(NO_3) \times H_2O$ hydrate.

11. The method of claim 9, wherein the one or more organic molecule isomers are the p-isomers.

12. The method of claim 11, wherein the p-isomers are p-xylene, p-ethylvinylbenzene, p-divinylbenzene or a combination thereof.

13. The method of claim 9, wherein the one or more organic molecules comprise pyridine, benzene, xylene, ethylvinylbenzene, divinylbenzene or a combination thereof.

14. The method of claim 9, wherein o-xylene, m-xylene, o-divinylbenzene, m-divinylbenzene, o-ethylvinylbenzene and are m-ethylvinylbenzene excluded from the porous microwaved Mg(II) coordination polymer.

15. The method of claim 9, wherein the method further comprises adding KOH to the reaction chamber in addition to the 2,4-pyridine carboxylic acid.

16. The composition made by the method of claim 9.

17. A porous coordination polymer comprising:
metal complexes formed by coordination bonding between Mg (II) and 2,4-pyridinedicarboxylic, wherein the porous coordination polymer has a pore structure formed by integration of a plurality of the metal complexes that selectively binds a p-isomer of an organic molecule.

18. The porous coordination polymer of claim 17, wherein the pore structure has a diameter of about 2 nm.

* * * * *

UNITED STATES PATENT AND TRADEMARK OFFICE
CERTIFICATE OF CORRECTION

PATENT NO. : 10,183,235 B2
APPLICATION NO. : 15/532647
DATED : January 22, 2019
INVENTOR(S) : Simon M. Humphrey

Page 1 of 1

It is certified that error appears in the above-identified patent and that said Letters Patent is hereby corrected as shown below:

In the Claims

Column 12, Line 33, Claim 17, should read as:
"between Mg (II) and 2,4-pyridinedicarboxylic acid, wherein"

Signed and Sealed this
Nineteenth Day of March, 2019

Andrei Iancu
*Director of the United States Patent and Trademark Office*